United States Patent [19]

Cohen et al.

[11] Patent Number: 5,663,358
[45] Date of Patent: Sep. 2, 1997

[54] PROCESS FOR THE PREPARATION OF ORGANOSILICON DISULFIDE COMPOUNDS

[75] Inventors: Martin Paul Cohen, Fairlawn; Lawson Gibson Wideman, Tallmadge, both of Ohio

[73] Assignee: The Goodyear Tire & Rubber Company, Akron, Ohio

[21] Appl. No.: 589,283

[22] Filed: Jan. 22, 1996

[51] Int. Cl.$^6$ ............... C07D 277/80; C07F 5/02; C07F 7/08
[52] U.S. Cl. ............ 548/166; 556/469; 556/478; 556/482; 556/487; 556/489
[58] Field of Search ............ 548/166; 556/469, 556/478, 482, 487, 489

[56] References Cited

U.S. PATENT DOCUMENTS

| | | | |
|---|---|---|---|
| 3,768,537 | 10/1973 | Hess et al. | 152/330 |
| 3,842,111 | 10/1974 | Meyer-Simon | 260/448.2 |
| 4,390,648 | 6/1983 | Stacy | 523/216 |
| 4,820,751 | 4/1989 | Takeshita et al. | 523/215 |
| 5,440,064 | 8/1995 | Agostini et al. | 556/427 |

FOREIGN PATENT DOCUMENTS

| | | | |
|---|---|---|---|
| 0676443 | 3/1995 | European Pat. Off. | C08K 3/36 |
| 124400 | 6/1984 | Japan | C08L 21/00 |

OTHER PUBLICATIONS

Brzezinska, E, and Ternay, Andrew L, *J. Org. Chem.* 1994, 59, 8239–8244, "Disulfides. 1. Synthesis Using 2,2',–Dithiobis(benzothiazole):".

The Abstract for JP 7228588–A relates to sulfur–containing organosilicon compounds which are prepared by reacting sodium sulfite with sulfur to give sodium polysulfide followed by an in situ reaction with a haloalkoxysilane.

*Primary Examiner*—Johann Richter
*Assistant Examiner*—Jane C. Oswecki
*Attorney, Agent, or Firm*—Bruce J. Hendricks

[57] ABSTRACT

The present invention relates to a process for the preparation of organo silicon disulfide compounds. The process involves reacting a mercaptoalkoxysilane with a sulfenamide compound.

14 Claims, No Drawings

PROCESS FOR THE PREPARATION OF ORGANOSILICON DISULFIDE COMPOUNDS

BACKGROUND OF THE INVENTION

The present invention relates to a process for the preparation of organosilicon disulfide compounds. Organosilicon disulfides are known adhesion promoters in sulfur-vulcanizable rubber mixtures reinforced with inorganic materials such as glass $SiO_2$, aluminosilicates and carbon black. For example, in GB 1,484,909, there is disclosed a process for the preparation of organo trialkoxysilane disulfides. In accordance with the teachings of this reference, mercaptopropyl trimethoxy silane or mercaptopropyl triethoxy silane is reacted with sulfuryl chloride in an inert solvent at temperatures of from 0° to 100°. The disulfide is then obtained by fractional distillation. The yields of desired product range in the neighborhood of 63 to 65 percent of theoretical.

U.S. Pat. No. 3,842,111 discloses a method for the preparation of organosilicon disulfide compounds by oxidizing mercaptoalkoxysilanes. Representative oxidizing agents include oxygen, chlorine, halogens of atomic weight 35 to 127, nitric oxide, sulfuryl chloride and sulfoxides.

Generally speaking, organosilicon disulfide compounds are very expensive and, with the increasing interest in silica-reinforced vulcanizable rubber, more cost-efficient methods of preparing these compounds are needed.

SUMMARY OF THE INVENTION

The present invention relates to a process for the preparation of a organosilicon disulfide compounds. The present invention may be used to prepare symmetrical organosilicon disulfide compounds of the formula

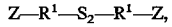

$$Z-R^1-S_2-R^1-Z, \quad \text{I}$$

unsymmetrical organosilicon disulfide compounds of the formula

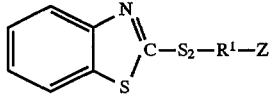

and mixtures thereof, wherein Z is selected from the group consisting of

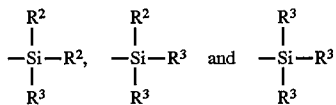

wherein $R^2$ may be the same or different and is independently selected from the group consisting of an alkyl group having 1 to 4 carbons and phenyl; $R^3$ may be the same or different and is independently selected from the group consisting of alkoxy groups having 1 to 8 carbon atoms and cycloalkoxy groups with 5 to 8 carbon atoms; and $R^1$ is selected from the group consisting of a substituted or unsubstituted alkylene group having a total of 1 to 18 carbon atoms and a substituted or unsubstituted arylene group having a total of 6 to 12 carbon atoms.

DETAILED DESCRIPTION OF THE INVENTION

There is disclosed a process for the preparation of organosilicon disulfide compounds comprising reacting (a) a sulfenamide compound of the formula

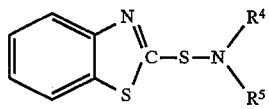

where $R^4$ is selected from the group consisting of hydrogen, acyclic aliphatic groups having from 1 to 10 carbon atoms and cyclic aliphatic groups having from 5 to 10 carbon atoms; and $R^5$ is selected from the group consisting of acyclic aliphatic groups having 1 to 10 carbon atoms and cyclic aliphatic groups having from 5 to 10 carbon atoms; with (b) a mercaptosilane compound of the formula

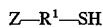

$$Z-R^1-SH \quad \text{IV}$$

wherein Z is selected from the group consisting of

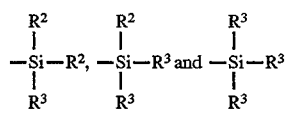

wherein $R^2$ may be the same of different and is independently selected from the group consisting of an alkyl group having 1 to 4 carbon and phenyl; $R^3$ may be the same of different and is independently selected from the group consisting of alkoxy groups having 1 to 8 carbon atoms and cycloalkoxy groups with 5 to 8 carbon atoms; and $R^1$ is selected from the group consisting of a substituted or unsubstituted alkylene group having a total of 1 to 18 carbon atoms and a substituted or unsubstituted arylene group having a total of 6 to 12 carbon atoms.

The present invention relates to a process for the preparation of organosilicon disulfide compounds. Representative organosilicon disulfide compounds of formula I which may be prepared in accordance with the present invention include 2,2'-bis(trimethoxysilylethyl) disulfide; 3,3'-bis(trimethoxysilylpropyl) disulfide; 3,3'-bis(triethoxysilylpropyl) disulfide; 2,2'-bis(triethoxysilypropyl) disulfide; 2,2'-bis(tripropoxysilylethyl) disulfide; 2,2'-bis(tri-sec-butoxysilylethyl) disulfide; 2,2'-bis(tri-t-butoxysilylethyl) disulfide; 3,3'-bis(triisopropoxysilylpropyl) disulfide; 3,3'-bis(trioctoxysilylpropyl) disulfide; 2,2'-bis(2'-ethylhexoxysilylethyl) disulfide; 2,2'-bis(dimethoxy ethoxysilylethyl) disulfide; 3,3'-bis(methoxyethoxypropoxysilylpropyl) disulfide; 3,3'-bis(dimethoxymethylsilylpropyl) disulfide; 3,3'-bis(methoxy dimethylsilylpropyl) disulfide; 3,3'-bis(diethoxymethylsilylpropyl) disulfide; 3,3'-bis(ethoxydimethylsilylpropyl) disulfide; 3,3'-bis(cyclohexoxy dimethylsilylpropyl) disulfide; 4,4'-bis(trimethoxysilylbutyl) disulfide; 3,3'-bis(trimethoxysilyl-3-methylpropyl) disulfide; 3,3'-bis(tripropoxysilyl-3-methylpropyl) disulfide; 3,3'-bis(dimethoxy methylsilyl-3-ethylpropyl) disulfide; 3,3'-bis(trimethoxysilyl-2-methylpropyl) disulfide; 3,3'-bis(dimethoxyphenylsilyl-2-methylpropyl) disulfide; 3,3'-bis(trimethoxysilylcyclohexyl) disulfide; 12,12'-bis(trimethoxysilyldodecyl) disulfide; 12,12'-bis(triethoxysilyldodecyl) disulfide; 18,18'-bis(trimethoxysilyloctadecyl) disulfide; 18,18'-bis(methoxydimethylsilyloctadecyl) disulfide; 2,2'-bis(trimethoxysilyl-2-methylethyl) disulfide; 2,2'-bis (tripropoxysilyl-2-methylethy) disulfide; 2,2'-bis (trioctoxysilyl-2-methylethyl) disulfide; 2,2'-bis (trimethoxysilyl-phenyl) disulfide; 2,2'-bis(triethoxysilylphenyl) disulfide; 2,2'-bis(trimethoxysilyl-tolyl)disulfide; 2,2'-bis(triethoxysilyl-tolyl)disulfide; 2,2'-bis (trimethoxysilyl-methyl tolyl) disulfide; 2,2'-bis (triethoxysilyl-methyl tolyl) disulfide; 2,2'-bis (trimethoxysilyl-ethyl phenyl) disulfide; 2,2'-bis (triethoxysilyl-ethyl phenyl) disulfide; 2,2'-bis (trimethoxysilyl-ethyl tolyl) disulfide; 2,2'-bis (triethoxysilyl-ethyl tolyl) disulfide; 3,3'-bis (trimethoxysilyl-propyl phenyl) disulfide; 3,3'-bis (triethoxysilyl-propyl phenyl) disulfide; 3,3'-bis (trimethoxysilyl-propyl tolyl) disulfide; and 3,3'-bis (triethoxysilyl-propyl tolyl) disulfide.

Representative organosilicon disulfide compounds of formula II which may be prepared in accordance with the present invention include 2-benzothiazyl-(3-triethoxysilyl) propyl disulfide; 2-benzothiazyl-(2-trimethoxysilylethyl) disulfide; 2-benzothiazyl-(3-trimethoxysilylpropyl) disulfide; 2-benzothiazyl-(2-triethoxysilylpropyl) disulfide; 2-benzothiazyl-(2-tripropoxysilylethyl) disulfide; 2-benzothiazyl-(2-tri-sec-butoxysilylethyl) disulfide; 2-benzothiazyl-(2-tri-t-butoxysilylethyl) disulfide; 2-benzothiazyl-(3-triisopropoxysilylpropyl) disulfide; 2-benzothiazyl-(3-trioctoxysilylpropyl) disulfide; 2-benzothiazyl-(2-ethylhexoxysilylethyl) disulfide; 2-benzothiazyl-(2-dimethoxy ethoxysilylethyl) disulfide; 2-benzothiazyl-(3-methoxyethoxypropoxysilylpropyl) disulfide; 2-benzothiazyl-(3-dimethoxymethylsilylpropyl) disulfide; 2-benzothiazyl-(3-methoxy dimethylsilylpropyl) disulfide; 2-benzothiazyl-(3-diethoxymethylsilylpropyl) disulfide; 2-benzothiazyl-(3-ethoxydimethylsilylpropyl) disulfide; 2-benzothiazyl-(3-cyclohexoxy dimethylsilylpropyl) disulfide; 2-benzothiazyl-(4-trimethoxysilylbutyl) disulfide; 2-benzothiazyl-(3-trimethoxysilyl-3-methylpropyl) disulfide; 2-benzothiazyl-(3-tripropoxysilyl-3-methylpropyl) disulfide; 2-benzothiazyl-(3-dimethoxy methylsilyl-3-ethylpropyl) disulfide; 2-benzothiazyl-(3-trimethoxysilyl-2-methylpropyl) disulfide; 2-benzothiazyl-(3-dimethoxyphenylsilyl-2-methylpropyl) disulfide; 2-benzothiazyl-(3-trimethoxysilylcyclohexyl) disulfide; 2-benzothiazyl-(12-trimethoxysilyldodecyl) disulfide; 2-benzothiazyl-(12-triethoxysilyldodecyl) disulfide; 2-benzothiazyl-(18-trimethoxysilyloctadecyl) disulfide; 2-benzothiazyl-(18-methoxydimethylsilyloctadecyl) disulfide; 2-benzothiazyl-(2-trimethoxysilyl-2-methylethyl) disulfide; 2-benzothiazyl-(2-tripropoxysilyl-2-methylethyl) disulfide; 2-benzothiazyl-(2-trioctoxysilyl-2-methylethyl) disulfide; 2-benzothiazyl-(2-trimethoxysilyl-phenyl) disulfide; 2-benzothiazyl-(2-triethoxysilyl-phenyl) disulfide; 2-benzothiazyl-(2-trimethoxysilyl-tolyl)disulfide; 2-benzothiazyl-(2-triethoxysilyl-tolyl)disulfide; 2-benzothiazyl-(2-trimethoxysilyl-methyl tolyl) disulfide; 2-benzothiazyl-(2-triethoxysilyl-methyl tolyl) disulfide; 2-benzothiazyl-(2-trimethoxysilyl-ethyl phenyl) disulfide; 2-benzothiazyl-(2-triethoxysilyl-ethyl phenyl) disulfide; 2-benzothiazyl-(2-trimethoxysilyl-ethyl tolyl) disulfide; 2-benzothiazyl-(2-triethoxysilyl-ethyl tolyl) disulfide; 2-benzothiazyl-(3-trimethoxysilyl-propyl phenyl) disulfide; 2-benzothiazyl-(3-triethoxysilyl-propyl phenyl) disulfide; 2-benzothiazyl-(3-trimethoxysilyl-propyl tolyl) disulfide; and 2-benzothiazyl-(3-triethoxysilyl-propyl tolyl) disulfide.

With reference to formulas I and II, preferably $R^1$ is a alkylene group having 1 to 3 carbon atoms Z is

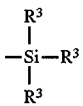

and $R^3$ is an alkoxy group having from 1 to 3 carbon atoms.

The desired products are prepared by reacting a sulfenamide compound of formula III with a mercaptosilane compound of formula IV. Representative examples of compounds of formula III include N-cyclohexyl-2-benzothiazylsulfenamide, N-t-butyl-2-benzothiazylsulfenamide, N,N-dicyclohexyl-2-benzothiazylsulfenamide, N-isopropyl-2-benzothiazylsulfenamide, N,N-dimethyl-2-benzothiazylsulfenamide, N,N-diethyl-2-benzothiazylsulfenamide, N,N-diproply-2-benzothiazylsulfenamide, N,N-diisopropyl-2-benzothiazylsulfenamide and N,N-diphenyl-2-benzothiazylsulfenamide. Preferably, the sulfenamide is N-cyclohexyl-2-benzothiazylsulfenamide.

Representative examples of compounds of formula IV include 2-mercaptoethyl trimethoxysilane, 3-mercaptopropyl trimethoxysilane, 3-mercaptopropyl triethoxysilane, 2-mercaptopropyl triethoxysilane, 2-mercaptoethyl tripropoxysilane, 2-mercaptoethyl tri sec-butoxysilane, 3-mercaptopropyl tri-t-butoxysilane, 3-mercaptopropyl triisopropoxysilane; 3-mercaptopropyl trioctoxysilane, 2-mercaptoethyl tri-2'-ethylhexoxysilane, 2-mercaptoethyl dimethoxy ethoxysilane, 3-mercaptopropyl methoxyethoxypropoxysilane, 3-mercaptopropyl dimethoxy methylsilane, 3-mercaptopropyl methoxy dimethylsilane, 3-mercaptopropyl diethoxy methylsilane, 3-mercaptopropyl ethoxy dimethylslane, 3-mercaptopropyl cyclohexoxy dimethyl silane, 4-mercaptobutyl trimethoxysilane, 3mercapto-3-methylpropyltrimethoxysilane, 3-mercapto-3-methylpropyl-tripropoxysilane, 3-mercapto-3-ethylpropyl-dimethoxy methylsilane, 3-mercapto-2-methylpropyl trimethoxysilane, 3-mercapto-2-methylpropyl dimethoxy phenylsilane, 3-mercaptocyclohexyl-trimethoxysilane, 12-mercaptododecyl trimethoxy silane, 12-mercaptododecyl triethoxy silane, 18-mercaptooctadecyl trimethoxysilane, 18-mercaptooctadecyl methoxydimethylsilane, 2-mercapto-2-methylethyl-tripropoxysilane, 2-mercapto-2-methylethyl-trioctoxysilane, 2-mercaptophenyl trimethoxysilane, 2-mercaptophenyl triethoxysilane; 2-mercaptotolyl trimethoxysilane; 2-mercaptotolyl triethoxysilane; 2-mercaptomethyltolyl trimethoxysilane; 2-mercaptomethyltolyl triethoxysilane; 2-mercaptoethylphenyl trimethoxysilane; 2-mercaptoethylphenyl triethoxysilane; 2-mercaptoethyltolyl trimethoxysilane; 2-mercaptoethyltolyl triethoxysilane; 3-mercaptopropylphenyl trimethoxysilane; 3-mercaptopropylphenyl triethoxysilane; 3-mercaptopropyltolyl trimethoxysilane; and 3-mercaptopropyltolyl triethoxysilane.

With reference to formula IV, preferably Z is

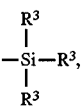

$R^3$ is an alkoxy group having from 1 to 3 carbon atoms and $R^1$ is an alkylene group having 2 to 3 carbon atoms.

The molar ratio of the compound of formula III to the compound of formula IV may range from 1:5 to 5:1. Preferably, the molar ratio ranges from 1:3 to 3:1 with a range of from 1:1 to 1:2 being particularly preferred. As can be appreciated by the teachings herein, by varying the molar ratio of the compound of formula III to the compound of formula IV, one produces varying weight percentage of the symmetrical organosilicon disulfide of formula I and the unsymmetrical organosilicon disulfide for formula II.

The reaction should be conducted in the absence of water because the presence of a alkoxysilane moiety may be hydrolysed by contact with water.

The reaction of the present invention may be conducted in the presence of an organic solvent. Suitable solvents which may be used include chloroform, dichloromethane, carbon tetrachloride, hexane, heptane, cyclohexane, xylene, benzene, dichloroethylene, trichloroethylene, dioxane, diisopropyl ether, tetrahydrofuran and toluene. As indicated above, care should be exercised to avoid the presence of water during the reaction. Therefore, none of the above solvent should contain any appreciable levels of water. Preferably, the organic solvent is chloroform, heptane, xylene, cyclohexane or toluene.

The reaction may be conducted over a variety of temperatures. Generally speaking, the reaction is conducted in a temperature ranging from 20° C. to 140° C. Preferably, the reaction is conducted at a temperature ranging from 50° C. to 90° C.

The process of the present invention may be conducted at a variety of pressures. Generally speaking, however, the reaction is conducted at a pressure ranging from 0.96 to 4.83 kg/cm².

EXAMPLE 1

Preparation of 2-Benzothiazyl-(3-Triethoxysilyl) Propyl Disulfide and Bis (3-Triethoxysilyl)Propyl Disulfide A 1-quart (0.946 l) glass reactor was charged with 400 ml of mixed xylenes, 25.1 g (0.10 mole) of N-cyclohexyl-2-benzothiazolesulfenamide, 23.8 g (0.10 mole) of 3-mercaptopropyltriethoxysilane and shaken for a few minutes, wherein an exotherm to 32° C. was observed and a thick off-white-to-yellow precipitate began to form. The reaction was stirred for 4 hours, filtered and dried under 29 inches of Hg vacuum, to give 18 g of a liquid product containing 27.2 percent by weight of 2-benzothiazyl-(3-triethoxysilyl)propyl disulfide and 42.7 percent by weight of bis (3-triethoxysilyl)propyl disulfide, with 19 percent by weight of starting material as determined by GPC and mass spectrometric analysis.

EXAMPLE 2

Preparation of Bis(3-Triethoxysilyl)Propyl Disulfide

A 1-quart (0.946l) glass reactor was charged with 400 ml of mixed xylenes, 25.1 g (0.10 mole) of N-cyclohexyl-2-benzothiazolesulfenamide, 47.6 g (0.20 mole) of 3-mercaptopropyltriethoxysilane and shaken for a few minutes, wherein an exotherm to 33° C. was observed and a thick off-white-to-yellow-brown precipitate began to form. The reaction was stirred for 4 hours, filtered and stripped under 29 inches of Hg vacuum, to give 44.5 g of a liquid product containing 98 percent by weight of bis 3-triethoxysilyl)propyl disulfide, as determined by GPC and mass spectrometric analysis. The precipitate weighed 38.4 g and was determined to be mercaptobenzothiazole.

EXAMPLE 3

Preparation of Bis(3-Triethoxysilyl)Propyl Disulfide

A 1-quart (0.946l) glass reactor was charged with 400 ml of mixed xylenes, 23.9 g (0.10 mole) of N-t-butyl-2-benzothiazolesulfenamide, 47.6 g (0.20 mole) of 3-mercaptopropyltriethoxysilane and shaken for a few minutes, wherein an exotherm to 33° C. was observed and a thick off-white-to-yellow-brown precipitate began to form. The reaction was stirred for 4 hours, filtered and stripped under 29 inches of Hg vacuum, to give 40.0 g of a liquid product containing 97 percent by weight of bis (3-triethoxysilyl)propyl disulfide, as determined by GPC and mass spectrometric analysis. The precipitate weighed 30.6 g and was determined to be mercaptobenzothiazole.

What is claimed is:

1. A process for the preparation of organosilicon disulfide compounds of the formula

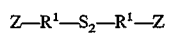

$$Z-R^1-S_2-R^1-Z \qquad I$$

or

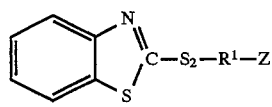

$$\text{II}$$

comprising reacting (a) a sulfenamide compound of the formula

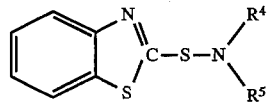

$$\text{III}$$

where $R^4$ is selected from the group consisting of hydrogen, acyclic aliphatic groups having from 1 to 10 carbon atoms and cyclic aliphatic groups having from 5 to 10 carbon atoms; and $R^5$ is selected from the group consisting of acyclic aliphatic groups having 1 to 10 carbon atoms and cyclic aliphatic groups having from 5 to 10 carbon atoms; with (b) a mercaptosilane compound of the formula

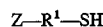

$$Z-R^1-SH \qquad IV$$

wherein Z is selected from the group consisting of

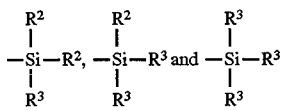

wherein $R^2$ may be the same or different and is independently selected from the group consisting of an alkyl group having 1 to 4 carbon atoms and phenyl; $R^3$ may be the same or different and is independently selected from the group consisting of alkoxy groups having 1 to 8 carbon atoms and cycloalkoxy groups with 5 to 8 carbon atoms; and $R^1$ is selected from the group consisting of a substituted or unsubstituted alkylene group having a total of 1 to 18 carbon atoms and a substituted or unsubstituted arylene group having a total of 6 to 12 carbon atoms.

2. The process of claim 1 wherein

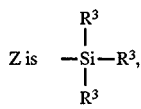

$R^3$ selected from the group consisting of alkoxy groups having 1 to 2 carbon atoms and $R^1$ is an alkylene group having 1 to 3 carbon atoms.

3. The process of claim 1 wherein the molar ratio of the compound of formula III to the compound of formula IV ranges from 1:5 to 5:1.

4. The process of claim 2 wherein the molar ratio of the compound of formula III to the compound of formula IV ranges from 1:3 to 3:1.

5. The process of claim 1 wherein said organosilicon disulfide of formula I is selected from the group consisting of 2,2'-bis(trimethoxysilylethyl) disulfide; 3,3'-bis (trimethoxysilylpropyl) disulfide; 3,3'-bis (triethoxysilylpropyl) disulfide; 2,2'-bis (tripropoxysilylethyl) disulfide; 2,2'-bis (triethoxysilylpropyl) disulfide; 2,2'-bis(tri-sec-butoxysilylethyl) disulfide; 2,2'-bis(tri-t-butoxyethyl) disulfide; 3,3'-bis(triisopropoxysilylpropyl) disulfide; 3,3'-bis(trioctoxysilylpropyl) disulfide; 2,2'-bis(2'-ethylhexoxysilylethyl) disulfide; 2,2'-bis(dimethoxy ethoxysilylethyl) disulfide; 3,3'-bis (methoxyethoxypropoxysilylpropyl) disulfide; 3,3'-bis (dimethoxymethylsilylpropyl) disulfide; 3,3'-bis(methoxy dimethylsilylpropyl) disulfide; 3,3'-bis (diethoxymethylsilylpropyl) disulfide; 3,3'-bis (ethoxydimethylsilylpropyl) disulfide; 3,3'-bis(cyclohexoxy dimethylsilylpropyl) disulfide; 4,4'-bis (trimethoxysilylbutyl) disulfide; 3,3'-bis(trimethoxysilyl-3-methylpropyl) disulfide; 3,3'-bis(tripropoxysilyl-3-methylpropyl) disulfide; 3,3'-bis(dimethoxy methylsilyl-3-ethylpropyl) disulfide; 3,3'-bis(trimethoxysilyl-2-methylpropyl) disulfide; 3,3'-bis(dimethoxyphenylsilyl-2-methylpropyl) disulfide; 3,3'-bis(trimethoxysilylcyclohexyl) disulfide; 12,12'-bis(trimethoxysilyldodecyl) disulfide; 12,12'-bis(triethoxysilyldodecyl) disulfide; 18,18'-bis (trimethoxysilyloctadecyl) disulfide; 18,18'-bis (methoxydimethylsilyloctadecyl) disulfide; 2,2'-bis (trimethoxysilyl-2-methylethyl) disulfide; 2,2'-bis (tripropoxysilyl-2-methylethyl) disulfide; 2,2'-bis (trioctoxysilyl-2-methylethyl) disulfide; 2,2'-bis (trimethoxysilyl-phenyl) disulfide; 2,2'-bis(triethoxysilyl-phenyl) disulfide; 2,2'-bis(trimethoxysilyl-tolyl) disulfide; 2,2'-bis(triethoxysilyl-tolyl) disulfide; 2,2'-bis (trimethoxysilyl-methyl-tolyl) disulfide; 2,2'-bis (triethoxysilyl-methyl-tolyl) disulfide; 2,2'-bis (trimethoxysilyl-ethyl phenyl) disulfide; 2,2'-bis (triethoxysilyl-ethyl phenyl) disulfide; 2,2'-bis (trimethoxysilyl-ethyl tolyl) disulfide; 2,2'-bis (triethoxysilyl-ethyl tolyl) disulfide; 3,3'-bis (trimethoxysilyl-propyl phenyl) disulfide; 3,3'-bis (triethoxysilyl-propyl phenyl) disulfide; 3,3'-bis (trimethoxysilyl-propyl tolyl) disulfide; and 3,3'-bis (triethoxysilyl-propyl tolyl) disulfide.

6. The process of claim 1 wherein said organosilicon disulfide of formula II is selected from the group consisting of 2-benzothiazyl-(3-triethoxysilyl)propyl disulfide; 2-benzothiazyl-(2-trimethoxysilylethyl) disulfide; 2-benzothiazyl-(3-trimethoxysilylpropyl) disulfide; 2-benzothiazyl-(2-triethoxysilylpropyl) disulfide; 2-benzothiazyl-(2-tripropoxysilylethyl) disulfide; 2-benzothiazyl-(2-tri-sec-butoxysilylethyl) disulfide; 2-benzothiazyl-(2-tri-t-butoxysilylethyl) disulfide; 2-benzothiazyl-(3-triisopropoxysilylpropyl) disulfide; 2-benzothiazyl-(3-trioctoxysilylpropyl) disulfide; 2-benzothiazyl-(2-2'-ethylhexoxysilylethyl) disulfide; 2-benzothiazyl-(2-dimethoxy ethoxysilylethyl) disulfide; 2-benzothiazyl-(3-methoxyethoxypropoxysilylpropyl) disulfide; 2-benzothiazyl-(3-dimethoxymethylsilylpropyl) disulfide; 2-benzothiazyl-(3-methoxy dimethylsilylpropyl) disulfide; 2-benzothiazyl-(3-diethoxymethylsilylpropyl) disulfide; 2-benzothiazyl-(3-ethoxydimethylsilylpropyl) disulfide; 2-benzothiazyl-(3-cyclohexoxy dimethylsilylpropyl) disulfide; 2-benzothiazyl-(4-trimethoxysilylbutyl) disulfide; 2-benzothiazyl-(3-trimethoxysilyl-3-methylpropyl) disulfide; 2-benzothiazyl-(3-tripropoxysilyl-3-methylpropyl) disulfide; 2-benzothiazyl-(3-dimethoxy methylsilyl-3-ethylpropyl) disulfide; 2-benzothiazyl-(3-trimethoxysilyl-2-methylpropyl) disulfide; 2-benzothiazyl-(3-dimethoxyphenylsilyl-2-methylpropyl) disulfide; 2-benzothiazyl-(3-trimethoxysilylcyclohexyl) disulfide; 2-benzothiazyl-(12-trimethoxysilyldodecyl) disulfide; 2-benzothiazyl-(12-triethoxysilyldodecyl) disulfide; 2-benzothiazyl-(18-trimethoxysilyloctadecyl) disulfide; 2-benzothiazyl-(18-methoxydimethylsilyloctadecyl) disulfide; 2-benzothiazyl-(2-trimethoxysilyl-2-methylethyl) disulfide; 2-benzothiazyl-(2-tripropoxysilyl-2-methylethyl) disulfide; 2-benzothiazyl-(2-trioctoxysilyl-2-methylethyl) disulfide; 2-benzothiazyl-(2-trimethoxysilyl-phenyl) disulfide; 2-benzothiazyl-(2-triethoxysilyl-phenyl) disulfide; 2-benzothiazyl-(2-trimethoxysilyl-tolyl)disulfide; 2-benzothiazyl-(2-triethoxysilyl-tolyl)disulfide; 2-benzothiazyl-(2-trimethoxysilyl-methyl tolyl) disulfide; 2benzothiazyl-(2-triethoxysilyl-methyl tolyl) disulfide; 2-benzothiazyl-(2-trimethoxysilyl-ethyl phenyl) disulfide; 2-benzothiazyl-(2-triethoxysilyl-ethyl phenyl) disulfide; 2-benzothiazyl-(2-trimethoxysilyl-ethyl-tolyl) disulfide; 2-benzothiazyl-(2-triethoxysilyl-ethyl tolyl) disulfide; 2-benzothiazyl-(3-trimethoxysilyl-propyl phenyl) disulfide; 2-benzothiazyl-(3-triethoxysilyl-propyl phenyl) disulfide; 2-benzothiazyl-(3-trimethoxysilyl-propyl tolyl) disulfide; and 2-benzothiazyl-(3-triethoxysilyl-propyl tolyl) disulfide.

7. The process of claim 1 wherein said sulfenamide compound of formula III is selected from the group consisting of N-cyclohexyl-2-benzothiazylsulfenamide, N-t-butyl-2-benzothiazylsulfenamide, N,N-dicyclohexyl-2-benzothiazylsulfenamide, N-isopropyl-2-benzothiazylsulfenamide, N,N-dimethyl-2-benzothiazylsulfenamide, N,N-diethyl-2-benzothiazylsulfenamide, N,N-dipropyl-2-benzothiazylsulfenamide, N,N-diisopropyl-2-benzothiazylsulfenamide and N,N-diphenyl-2-benzothiazylsulfenamide.

8. The process of claim 1 wherein said compound of formula IV is selected from a group consisting of 2-mercaptoethyl trimethoxysilane, 3-mercaptopropyl trimethoxysilane, 2-mercaptopropyl triethoxysilane, 3-mercaptopropyl triethoxysilane, 2-mercaptoethyl tripropoxysilane, 2-mercaptoethyl tri sec-butoxysilane, 3-mercaptopropyl tri-t-butoxysilane, 3-mercaptopropyl triisopropoxysilane; 3-mercaptopropyl trioctoxysilane, 2-mercaptoethyl tri-2'-ethylhexoxysilane, 2-mercaptoethyl dimethoxy ethoxysilane, 3-mercaptopropyl methoxyethoxypropoxysilane, 3-mercaptopropyl dimethoxy methylsilane, 3-mercaptopropyl methoxy dimethylsilane, 3-mercaptopropyl diethoxy methylsilane, 3-mercaptopropyl ethoxy dimethylsilane, 3-mercaptopropyl cyclohexoxy dimethyl silane, 4-mercaptobutyl trimethoxysilane, 3-mercapto-3-methylpropyltrimethoxysilane, 3-mercapto-3- methylpropyl-tripropoxysilane, 3-mercapto-3-ethylpropyl-dimethoxy methylsilane, 3-mercapto-2-methylpropyl trimethoxysilane, 3-mercapto-2-methylpropyl dimethoxy phenylsilane, 3-mercaptocyclohexyl-trimethoxysilane, 12-mercaptododecyl trimethoxy silane, 12-mercaptododecyl triethoxy silane, 18-mercaptooctadecyl trimethoxysilane, 18-mercaptooctadecyl methoxydimethylsilane, 2-mercapto-2-methylethyl-tripropoxysilane, 2-mercapto-2-methylethyl-trioctoxysilane, 2-mercaptophenyl trimethoxysilane, 2-mercaptophenyl triethoxysilane; 2-mercaptotolyl trimethoxysilane; 2-mercaptotolyl triethoxysilane; 2-mercaptomethyltolyl trimethoxysilane; 2-mercaptomethyltolyl triethoxysilane; 2-mercaptoethylphenyl trimethoxysilane; 2-mercaptoethylphenyl triethoxysilane; 2-mercaptoethyltolyl trimethoxysilane; 2-mercaptoethyltolyl triethoxysilane; 3-mercaptopropylphenyl trimethoxysilane; 3-mercaptopropylphenyl triethoxysilane; 3-mercaptopropyltolyl trimethoxysilane; and 3-mercaptopropyltolyl triethoxysilane.

9. The process of claim 1 wherein the reaction is conducted in absence of water and in the presence of an organic solvent selected from the group consisting of chloroform, dichloromethane, carbon tetrachloride, hexane, heptane, cyclohexane, xylene, benzene, dichloroethylene, trichloroethylene, dioxane, diisopropyl ether, tetrahydrofuran and toluene.

10. The process of claim 1 wherein the reaction is conducted at a temperature ranging from 20° C. to 140° C.

11. The process of claim 10 wherein the reaction is conducted at a temperature ranging from 50° C. to 90° C.

12. The process of claim 1 wherein the reaction is conducted at a pressure ranging from 0.096 to 4.83 kg/cm$^2$.

13. The process of claim 5 wherein said organosilicon disulfide of formula I is 3,3'-bis(triethoxysilylpropyl) disulfide.

14. The process of claim 6 wherein said organosilicon disulfide of formula II is 2-benzothiazyl-(3-triethoxysilyl) propyl disulfide.

* * * * *